United States Patent [19]

Atabekov et al.

[11] Patent Number: 4,808,522
[45] Date of Patent: Feb. 28, 1989

[54] ENZYME IMMUNOASSAYS USING INORGANIC PYROPHOSPHATASE

[75] Inventors: Iosif G. Atabekov; Svetlana M. Avaeva; Alexandr A. Baikov; Alexandr V. Kulinich; Olga A. Mizenina; Vladimir N. Kasho; Irina N. Smirnova, all of Moscow, U.S.S.R.

[73] Assignee: Moskovsky Gosudarstvennx Universitet Imeni M. V. Lomonoso VA, U.S.S.R.

[21] Appl. No.: 855,507

[22] Filed: Apr. 23, 1986

[51] Int. Cl.$^4$ ............... G01N 33/535; C12Q 1/42
[52] U.S. Cl. ............................. 435/7; 435/21; 435/188
[58] Field of Search ..................... 435/7, 21, 188

[56] References Cited

U.S. PATENT DOCUMENTS

| | | | |
|---|---|---|---|
| 3,791,932 | 2/1974 | Schuurs | 435/7 |
| 3,879,262 | 4/1975 | Schuurs | 435/7 |
| 3,966,556 | 6/1976 | Rubenstein | 435/7 |
| 4,157,280 | 6/1979 | Halbert | 435/7 |
| 4,190,496 | 2/1980 | Rubenstein | 435/7 |
| 4,474,878 | 10/1984 | Halbert | 435/7 |

FOREIGN PATENT DOCUMENTS 2288312  5/1976  France.
1549069  7/1979  United Kingdom.

*Primary Examiner*—Esther M. Kepplinger
*Assistant Examiner*—Robert Benson
*Attorney, Agent, or Firm*—Ladas & Parry

[57] ABSTRACT

A method for determination of an antigen, which comprises preparation of a conjugate by way of cross-linking of an antibody with an inorganic pyrophosphatase, reacting the resulting conjugate with the antigen to be determined attached to the surface of a solid phase, separating the solid phase from the liquid one, reacting one of said phases with a substrate represented by a salt of pyrophosphoric acid. After carrying out the reaction, a color reagent incorporating a salt of molybdic acid, a surfactant, malachite green dye and a strong inorganic acid is added to the resulting reaction mixture and the content of the antigen is determined from its optical density.

3 Claims, No Drawings

ENZYME IMMUNOASSAYS USING INORGANIC PYROPHOSPHATASE

FIELD OF THE INVENTION

The present invention relates to the art of immunoenzymatic analysis and, more specifically, to a method for the determination of an antigen.

Methods for determination of an antigen are indispensable in diagnosis of diseases of human beings, animals and plants; in selection of plants and animals and in analysis of the environment.

For the determination of an antigen innumological methods are widely employed, which are based on a reaction of an antigen with an antibody. To increase the sensitivity of these methods antibodies labeled with radioactive or fluorescent compounds, or enzymes are used. The immunological method of analysis based on enzyme-labelled antibodies (immunoenzymatic analysis) becomes widely employed in recent years owing to a high sensitivity thereof and the fact that it eliminates the handling of substances harmful for human health.

BACKGROUND OF THE INVENTION

Known in the art are a number of methods of immunoenzymatic analysis. Most widely employed is the method of a heterogeneous immunoenzymatic analysis (ELISA), wherein the antigen to be determined is bound to a solid phase. Such combination is effected most frequently by adsorption of an antigen from the analyzed solution directly on the surface of a polymeric material or after a preliminary coating thereof with specific antibodies. Then the adsorbed antigen is reacted with a solution of these antibodies labeled with an enxyme (conjugate) to ensure the attachment of the conjugate to the solid phase. Thereafter, the solid phase is separated from the liquid one and one of the phases is analyzed to. The concentration of the analyzed antigen can be calculated from the value of enzymatic activity (cf. U.S. Pat. No. 3,720,760). However, this method necessitates preparation of a specific conjugate for every antigen to be determined.

To ensure the versatile character of the conjugate, it is obtained with the use of anti-species antibodies. In this case, specific antibodies are added to the antigen combined with the solid phase, followed by the addition of a conjugate of an enzyme containing the anti-species antibodies which have been obtained against the species employed for the preparation of specific antibodies (British Patent No. 1,549,069).

Particular methods, wherein these general principles are employed, are distinguished by types of the enzyme employed for the preparation of a conjugate. Properties of the enzyme define to a considerable extent the possibilities of the specific ELISA method, sensitivity and costs of the analysis in the first place. Desirable properties of the enzyme are its high specific activity and stability in storage. Previously employed for these purposes were alkaline phosphate, peroxidase, $\beta$-galactosidase, lysozyme, $\Delta_5$,3-ketosteriodisomerase, $\alpha$-amylase, glucosooxidase, and some others. Most widely employed are alkaline phosphatase, peroxydase and $\beta$-galactosidase.

An important characteristic of the ELISA method resides also in the type of a substrate employed for the determination of the enzymatic activity. The enzyme defines, to a considerable extent, the selection of a substrate, but the majority of enzymes allow certain variations in the substrate structure. In this case a high sensitivity of the determination of the product of substrate hydrolysis, low costs and stability thereof in storage are desirable.

The substrate for conjugates containing alkaline phosphatase is most frequently P-nitrophenylphosphate (cf. U.S. Pat. No. 3,879,262). The enzyme—alkaline phosphatase has a high specific activity, but it is insufficiently stable in storage. The product of hydrolysis of p-nitrophenylphosphate is of a light yellow colour which is substantially imperceptible by a human eye. For this reason a measuring instrument is indispensable.

Peroxidase is frequently employed for the preparation of conjugates in the ELISA method due to its low cost (cf. U.S. Pat. No. 3,791,932). However, it has a low specific activity so that the method based thereon has a low sensitivity. Furthermore, some substrates for peroxidase exhibit carcinogenic properties.

$\beta$-Galactosidase has a high activity and stability in storage. p-Nitrophenyl esters are used as it's substrates, which upon hydrolysis display a light yellow colour slightly perceptible by the human eye (cf. French Patent No. 2,288,312).

Substrates or alkaline phosphates, peroxidase and $\beta$-galactosidase employed in the immunoenzymatic analysis are unstable in aqueous solutions and have a high production cost, while substrates of alkaline phosphatase and $\beta$-galactosidase are also unstable in a long-term storage in the dry form.

Therefore, the prior art methods for the determination of an antigen do not ensure simultaneously a high sensitivity of analysis, necessitate the use of expensive reagents for the analysis, as well as sophisticated instruments, so that they can be used only in specialized laboratories.

It is an object of the present invention to provide a method for the determination of an antigen which would have a high sensitivity, especially in a visual determination of the antigen, which would be based on the use of stable reagents and, for this reason, could be accessible to a broad range of consumers.

SUMMARY OF THE INVENTION

This object is accomplished by a method for the determination of an antigen, comprising preparation of a conjugate by way of cross-linking of an antibody with an enzyme; combining the antigen to be determined with a solid phase; reacting the abovementioned conjugate with the determined antigen bound to the solid phase with the formation of solid and liquid phases; separation of the solid and liquid phases; reacting one of the phases with a substrate and determination of the amount of the antigen from its enzymatic activity. According to the present invention, the method is characterized in that in the preparation of the conjugate as the enzyme an inorganic pyrophosphatase (pyrophosphate phosphohydrolase EC 3.6.1.1) is used.

This object is accomplished by a method for the determination of an antigen consisting in the steps of:

preparation of a conjugate by way of cross-linking of an antibody with an inorganic pyrophosphatase;

binding the antigen to be determined with a solid phase;

reacting the above-mentioned conjugate with the antigen to be determined bound to the solid phase with the formation of solid and liquid phases;

separation of solid and liquid phases;

reacting one of the phases with a substrate and determination of the amount of the antigen by the values of its enzymatic activity.

The present invention makes it possible to increase the stability of the conjugate of antibodies when the enzyme is at elevated temperatures, since the inorganic pyrophosphatase exhibits a high thermal stability and withstands heating of up to 80° C.

According to the present invention, after reacting one of the phases with the substrate it is advisable to introduce into the reaction mixture a color reagent comprising a strong 3–7.5N inorganic acid containing the following components, percent by mass: a salt of molybdic acid-0.75–4.5, a surfactant-0.05–0.3, malachite green dye-0.025–0.25. This ensures a high sensitivity of the analysis in the visual determination of optical density.

In accordance with the present invention, it is advisable to use, as the substrate, a salt of pyrophosphoric acid. This salt has a sufficient solubility and can be, for example, sodium pyrophosphate, potassium pyrophosphate or ammonium pyrophosphate. This salt of pyrophosphoric acid is used in small amounts, since the Michaelis constant for an inorganic pyrophosphatase is equal to only several micromoles per liter. Furthermore, in comparison with known substrates employed in the immunoenzymatic analysis, a salt of pyrophosphoric acid is more stable in a long-term, storage. The concentration of this salt in the method according to the present invention is equal to 0.2–0.5 mM.

According to the present invention, the inorganic pyrophosphatase should be preferably isolated from *Escherichia coli* by way of a heat-treatment of a cell homogenate at a temperature of 83° to 93° C. and chromatographing on 1,6-diaminohexylagarose. As a result, the procedure for isolation of the above-specified enzyme becomes substantially simplified.

DETAILED DESCRIPTION OF THE INVENTION

In the first step of the process a conjugate of antibodies with an enzyme is obtained an inorganic pyrophosphate is used as the enzyme in the method according to the present invention an inorganic pyrophosphatase is used. This enzyme is well known and described in the literature in detail (Josse J., Wong S. C. K. The Enzymes, v.4, pp. 495–527/1971/; Butler L. G., p. 529–541). In the present invention the inorganic pyrophosphatase isolated from *Escherichia coli* is used. A method for recovering this enzyme is described in the literature (cf. Wong S. C. K., Hall D. C., Josse J., J. Biol. Chem., v. 245, p. 4335/1970/). An important advantage of this enzyme is its exceptional thermal stability. Thus, it withstands heating at the temperature of 80° C. for one hour and is stable in storage for 2 years at room termperature. The molecular mass of the enzyme is equal to 120,000 Dalton; it consists of 6 identical subunits, each of them having an active center. The catalytic activity of the enzyme at the temperature of 25° C. is about 2,400 $s^{-1}$. These properties of the enzyme make it highly effective in the determination of an antigen in the immunoenzymatic analysis.

To obtain a conjugate, an aqueous solution of a mixture of the inorganic pyrophosphatase and antibodies of bifunctional cross-linking agent (glutaric aldehyde) is added and the mixture is incubated therewith for a specified period of time. The resulting conjugate is separated from the starting compounds by means of gel-filtration.

Then, an antibody specific to the antigen being determined is bound to a solid phase; as the latter use can be made of the surface of a polymeric microplate for the immunoenzymatic analysis or another similar device. To this end, the surface is contacted with the antibody solution, whereby the latter gets adsorbed on the surface.

The reaction of the conjugate with the antigen to be determined combined with the solid phase is carried out in two ways, depending on the character of the antibody employed for the preparation of the conjugate. If the antibody is specific in relation to the anitgen to be determined, the solid phase is contacted with the conjugate solution, whereby it gets bound with the solid phase in an amount proportional to the amount of the antigen being determined. If the antibody is an anti-species one in relation to the specific antibody, the conjugate is reacted with the antibody in two stages. In the first stage the solid phase with the combined antigen is contacted with the solution of the specific antibody, wherefore the antibody is bound to the antigen. Then the solid phase is contacted with the solution of the conjugate so that the latter gets bound to the specific antibody in an amount proportional to the amount of the antigen being determined.

After carrying out the reaction of the conjugate with the antigen to be determined, the liquid and solid phases are separated and one of them is contacted with a solution of a substrate; as the latter a salt of pyrophosphoric acid labeled with [$^{32}P$] is used. After a certain period of time the [$^{32}P$] phosphate formed in hydrolysis of the substrate by the inorganic pyrophosphatase is determined. Finally, the radioactivity of [$^{32}P$] phosphate is determined and by its value the amount of the antigen in the sample is established.

In one aspect the invention provides a method, wherein after carrying out the reaction of one of the phases with the substrate a colour reagent is added into the reaction mixture; strong 3–7.5N inorganic acid incorporating the following components, percent by mass: a salt of molybdic acid-07.5–4.5, a surfactant-0.05–0.3, malachite green dye-0.025–0.25 is used as the color reagent.

Any salt possessing a sufficient solubility, e.g. ammonium salt, may be used as the salt of molybdic acid. The optimal concentration of this salt in the method according to the present invention is equal to 1.5% by mass. At a concentration below 0.75% by mass the optical density and, hence, the method's sensitivity, is lowered. At a concentration above 4.5% by mass the optical density is considerably increased in the absence of the determined antigen, thus lowering the sensitivity, especially in analysis of minor amounts of the antigen being determined. Twin-20, Triton X-305 and Sterox may be used as the surfactant. Its optimal concentration is 0.2% by mass; in this case the system remains transparent in the measurement of the optical density of up to 5 units. Lowering the surfactant concentration below 0.05% by mass decreases the upper limit of the optical density to which the optical transparency of the system is retained, while elevation of the concentration above 0.3% by mass decreases the optical density in the presence of the antigen to be determined.

The optimal concentration of malachite green dye is 0.085% by mass. Reducing its concentration below 0.025% by mass lowers the optical density in the presence of the determined antigen, while increasing its concentration above 0.25% by mass considerably raises the optical density in the absence of the antigen being determined.

As the acid in the method according to the present invention use can be made of sulphuric acid, hydrochloric acid and perchloric acid. Sulphuric acid in the concentration of 5N is optimal. Lowering the acid concentration below 3N or increasing thereof above 7.5N reduces the optical density in the presence of the antigen being determined.

The effect of the colour reagent is based on its reaction with the phosphate formed from the substrate. At the acid concentrations employed in the method according to the present invention a good solubility of malachite green is attained and no residue is formed.

Owing to the addition of the colour reagent, the reaction mixture acquires a blue-green colour. The extinction coefficient of the resulting coloured compound is at least 50,000 $M^{-1}cm^{-1}$. In the absence of the antigen in the analyzed sample the colour is pale yellow which ensures a high contrast. This colour change ensures a high sensitivity of the analysis in the visual assessment of its results.

A salt of pyrophosphoric acid in a concentration of 0.02–0.5 mM is used as the substrate. The optimal concentration is 0.05 mM. At a concentration of the salt of pyrophosphoric acid of less than 0.02 mM the optical density is considerably lowered in the presence of the determined antigen, while at a concentration above 0.5 mM the optical density in the absence of the antigen is considerably increased. The use of a salt of pyrophosphoric acid as the substrate is advantageous as it is considerably less expensive than many other substrates employed for the immunoenzymatic analysis. Furthermore, it is highly stable in the dry form for not less than 1 year in an aqueous solution.

As it has been mentioned hereinbefore, for the preparation of the conjugate an inorganic pyrophosphatase is used. It is advisable to use the pyrophosphatase obtained from cells of *Escherichia coli* by way of homogenization thereof and a heat-treatment of the cell homogenate at a temperature within the range of 83° to 93° C., followed by chromatographing it on 1,6-diaminohexylagarose. This makes it possible to substantially simplify the procedure of isolation of the enzyme. The heat-treatment of the cell homogenate of *E. coli* at the above-mentioned temperature makes it possible to ensure a more complete separation of foreign proteins from the pyrophosphatase in this stage of the process. This is due to the fact that the inorganic pyrophosphatase better withstands the heat treatment at an elevated temperature than foreign porteins. The heat-treatment duration in the method according to the present invention is 2 minutes. The optimal heat-treatment temperature is in the range of 83°–85° C. At a temperature below 83° C. a greater amount of foreign proteins remains, while at a temperature above 93° C. inactivation of the inorganic pyrophosphatase is possible. Chromatographing on 1,6-diaminohexylagarose makes it possible to ensure an effective purification of the inorganic pyrophosphatase owing to the fact that its affinity to this sorbent is very high and it is eluted therefrom at a concentration of about 0.5M. The degree of purity of the resulting enzyme, according to the data of electrophoresis in a polyacrylamide gel, is above 90%.

The method according to the present invention makes it possible to determine antigens visually by optical density. The coloration is easily perceived 0.1 unit and is stable for a week. In the absence of an antigen the colour is pale yellow, while in the presence of an antigen it is blue-green. The molar extinction coefficient of the reaction product is about 50,000$M^{-1}cm^{-1}$ at 630 nm. The method according to the present invention does not necessitate an obligatory storage of the conjugate and substrate at a low temperature which is attained due to a high stability thereof. The high stability of the enzyme makes it possible to carry out the determination of the antigen at a temperature of 50° to 60° C. This considerably shortens the duration of anaylsis. The procedure of isolation of the enzyme, i.e. of the inorganic pyrophosphatase is quite simple and based on the use of a readily available raw material-*Escherichia coli*. The use of a salt of pyrophosphoric acid as a substrate makes it possible to lower the cost of analysis of an antigen. The method according to the present invention is readily accessible to a broad range of customers.

The best mode for carrying out the method for the determination of the antigen according to the present invention resides in the following.

An inorganic pyrophosphatase is the enzyme used for preparing a conjugate. This pyrophosphatase is recovered from cells of *Escherichia coli*. The suspension of a biomass of *Escherichia coli* in a buffer solution is treated in an apparatus for breaking cells and producing a homogenate. The resulting homogenate of cells is subjected to a heat treatment at the temperature of 85° C. for 2 minutes, whereafter the above-mentioned enzyme is precipitated with ammonium sulphate. The resulting precipitate is dissolved in water, the solution is dialyzed and chromatographed in a column with 1,6-diaminohexylagarose.

The thus-prepared inorganic pyrophosphatase is mixed with antibodies in the presence of glutaric aldehyde and maintained for about one hour at room temperature. The resulting mixture is chromatographed in a buffer solution. The eluate fractions containing the conjugate are combined.

A buffer solution containing antibodies specific in relation to the determined antigen is placed into wells of a microplate for the immunoenzymatic analysis. Then the solution of antibodies is removed, the microboard is rinsed with a buffer solution containing sodium chloride and Triton X-305 and a solution or a suspension of the determined antigen in a tris buffer containing Triton X-305 and albumin is placed into the wells of the microplate for three hours at the temperature of 37° C. On expiration of 3 hours the antigen solution or suspension is removed, the microplate is rinsed with a buffer solution containing sodium chloride and Triton X-305 and a solution of the conjugate of the inorganic pyrophosphatase with antibodies specific in relation to the determined antigen is placed into the wells of the microplate for 20 minutes at the temperature of 55° C. in the presence of a buffer substance, Triton X-305 and albumin. The solution of the conjugate is removed, the mircoplate is rinsed with water and a 0.05 mM solution of non-radiactive sodium pyrophosphate containing the buffer substance and magnesium chloride is placed into the wells of a microplate for 10 minutes at the temperature of 55° C., whereafter 0.05 ml of a colour reagent is added which comprises a solution of 1.5% by mass of ammonium molybdate, 0.085% by mass of malachite green and 0.2% by mass of Twin-20 in a 5N sulphuric acid and the optical density of the reaction mass is measured at 630 nm.

This embodiment has the following advantages. The use of the pyrophosphatase recovered from *Escherichia coli* imparts a greater stability to the conjugate owing to stability of the above-mentioned enzyme. The thermal treatment of the homogenate of *Escherichia coli* cells makes it possible to attain a high purity grade of the enzyme and a high yield thereof. The use of the colour reagent in this embodiment of the method according to the present invention ensures a contrast change of coloration depending on the content of the antigen being determined and, therefore, makes it possible to visually determine an antigen at a high sensitivity.

For a better understanding of the present invention some specific examples are given hereinbelow; Examples 1 through 5 illustrate the recovery of the enzyme; Example 6 illustrates preparation of the conjugate; Examples 7 through 23 illustrate determination of an antigen.

EXAMPLE 1

Isolation of inorganic pyrophosphatase

A suspension of 2 kg of a biomass of *Escherichia coli* in 6 l of a 0.05M buffer of tris-HCl, pH=7.2, containing 10 mM of $MgCl_2$ is treated in a homogenizer to break cells of the bacteria. The resulting cell homogenate is passed successively at the rate of 3.6 l/h through two heat-exchangers supplied with water so that the homogenizate temperature at the outlet of the first heat-exchanger be equal to 85° C. and at the outlet of the second to 10° C.; the time of passing the homogenizate through the first heat-exchanger is 2 minutes. The homogenate is centrifuged and the resulting pellet is separated and discarded. The supernatant liquid is added with ammonium sulphate to the saturation of 55%, centrifuged and the pellet is discarded; the supernatant liquid is added with ammonium sulphate up to the saturation of 75% and centrifuged. The pellet is dissolved in 200 ml of water; the solution is dialyzed against water and placed into a column (4×ᴋ50 cm) with 1,6-diaminohexylagarose. The column is eluted with a 0.05M buffer of tris-HCl containing $MgCl_2$ and NaCl; the concentration of $MgCl_2$ is maintained constant (1 mM) while the concentration of NaCl is increased from 0 to 0.8M, the column is washed with this buffer till description of the pyrophosphatase.

From 2 kg of the biomass of *Escherichia coli* 0.38 g of an inorganic pyrophosphatase with the specific activity of 500 U/mg at 25° C. is obtained.

The results obtained in each step of the isolation of the pyrophosphatase are presented in the following Table 1.

EXAMPLES 2 THROUGH 5

Isolation of inorganic pyrophosphatase

The isolation of the inorganic pyrophosphatase is carried out in a manner similar to that

TABLE 1

| Isolation of inorganic pyrophosphatase | | |
|---|---|---|
| Stage | Specific activity of the enzyme, U/ml | Yield, % |
| Homogenation of cells | 1.66 | 100 |
| Heat treatment | 13.3 | 92 |
| Fractionation with ammonium sulphate | 55.3 | 74 |
| Chromatography on 1,6-diaminohexylagarose | 500 | 56 |

TABLE 1-continued

| Isolation of inorganic pyrophosphatase | | |
|---|---|---|
| Stage | Specific activity of the enzyme, U/ml | Yield, % | described in the foregoing Example 1, but the temperature of water supplied into the first heat-exchanger is varied so that the temperature of the cell homogenate at the outlet of this heat-exhanger be within the range of from 80° to 93° C. The values of specific activity and yield of the enzyme are shown in Table 2 hereinbelow.

TABLE 2

| Homogenate temperature, °C. | Specific activity of the enzyme, U/mg | Yield, % |
|---|---|---|
| 80 | 350 | 60 |
| 83 | 430 | 54 |
| 88 | 550 | 52 |
| 93 | 570 | 31 |

EXAMPLE 6

Preparation of a conjugate of an inorganic pyrophosphatase with antibodies.

A mixture of 8 mg of antibodies recovered from a rabbit's blood serum by precipitation with polyethylene glycol and chromatography on DEAE-cellulose and 8 mg of an inorganic pyrophosphatase are dissolved in 8 ml of a 0.01M phosphate buffer with the pH=7.4 containing 0.15M of NaCl, added with 0.02 ml of a 25% solution of glutaric aldehyde in water and incubated for one hour at the temperature of 22° C. Then the mixture is chromatographed at the temperature of 4° C. in a column (2.5×80 cm) with Sephacryl S-300 in a 0.05M buffer of tris-HCl, pH=7.5, containing 0.1M NaCl and 1 mM of $MgCl_2$. The fractions of the first protein peak are combined and used for the determination of an antigen.

EXAMPLE 7

Determination of carnation mottle disease virus

Into wells of a polystyrene microplate for the immunoenzymatic analysis a solution of antibodies (10 μg/ml) specific to the virus of pink mottle disease in a carbonate buffer of pH=9.6 l is placed for 20 hours at the temperature of 4° C. On expiration of this time the solution of antibodies is removed, the microplates are rinsed with a 0.01M buffer of tris-HCl (pH=7.5) containing 0.15M of NaCl and a 0.1% of Triton X-305 and a suspension of the virus of carnation mottle disease of a known concentration is placed for 3 hours at the temperature of 37° C. into recesses of a microboard in a 0.01M buffer of tris-HCl (pH=7.4) containing 0.1% of Triton X-305 and 0.1% of albumin of bovine blood serum. On expiration of 3 hours the vrius suspension is removed, the microplates are rinsed with a 0.01M buffer of tris-HCl (pH=7.5) containing 0.15M of NaCl and 0.1% of Triton X-305, and a solution of a conjugate of the inorganic pyrophosphatase isolated as in Example 1 with antibodies specific in relation to the virus of carnation mottle disease prepared as described in Example 6 is placed into wells of a microplate for 20 minutes at the temperature of 55° C. in the concentration of 0.5 U/ml in a 0.01M buffer of tris-HCl (pH=7.5) containing 0.1% of Triton X-305 and 0.1% of bovine serum albumin. The solution of the conjugate is removed, the microplates are rinsed with water and a 0.05 mM solution of [$^{32}$P] sodium pyrophosphate in a .01M buffer of tris-HCl (pH=9.0) containing 5 mM of MgCl$_2$ is placed into wells of the microplate for 10 minutes at the temperature of 55° C., whereafter 60 μl of a 0.25M solution of ammonium molybdate and 14 μl of a 6N HCl are added thereto. After stirring, 0.3 ml of the resulting mixture are charged into a testtube and added with 0.3 ml of a mixture of isobutanol-benzene (1:1 by volume) and vigorously shaken. After separation of the aqueous and organic phases the radioactivity of 0.2 ml of the organic phase containing [$^{32}$P] pyrophosphate is measured by means of a liquid-scintillation counter. The thus-obtained data are given in Table 3 hereinbelow.

TABLE 3

| Concentration of the virus, ng/ml | Radioactivity of the organic phase, puls/min |
|---|---|
| 0 (control) | 450 |
| 1 | 710 |
| 2 | 995 |
| 4 | 1,450 |
| 10 | 2,810 |
| 20 | 4,520 |

This example illustrates the possibility of carrying out the analysis at an elevated temperature (55° C.) thus making it possible to shorten the time of incubation of microplates with solutions of the conjugate and the substrate as compared to those conventionally employed.

EXAMPLE 8

Determination of the carnation mottle virus disease with the use of colour reagent The procedure of Example 7 hereinbefore is substantially repeated, except that the solution of the conjugate and the solution of sodium pyrophosphate are kept in wells of the microplate for one hour at the temperature of 37° C.; as the substrate use is made of non-radiactive sodium pyrophosphate of the concentrations of 0.02, 0.05 and 0.5 mM; after carrying out the reaction of a conjugate combined with the surface of a solid phase with a substrate 0.05 ml of a colour reagent comprising a solution of 1.5% by mass of ammonium molybdate, 0.085% by mass of malachite green and 0.2% by mass of Twin-20 in a 5N sulphuric acid is added and the optical density of the reaction mixture is measured at 630 nm. The data for certain concentrations of the virus are given in Table 4.

TABLE 4

| Concentration of the virus, ng/ml | Optical density at specified concentrations of the substrate, mM | | |
|---|---|---|---|
| | 0.02 | 0.05 | 0.5 |
| 0 (control) | 0.052 | 0.069 | 0.201 |
| 1 | 0.121 | 0.160 | 0.308 |
| 2 | 0.193 | 0.251 | 0.401 |
| 4 | 0.317 | 0.416 | 0.582 |
| 10 | 0.583 | 0.761 | 0.989 |

The visual analysis has revealed that the coloration of the reaction medium is changed from a pale yellow in the absence of the virus to a bright blue at a high concentration of the virus. The coloration in samples with an optical density above 0.16 is certainly different from that in the control experiment.

EXAMPLES 9 THROUGH 20

Determination of the carnation mottle virus disease

The procedure of Example 8 is repeated using sodium pyrophosphate in the concentration of 0.05 mM and different concentrations of ammonium molybdate, a surfactant, malachite green dye and the acid. The virus concentration is 10 ng/ml. The data thus obtained are shown in Table 6 hereinbelow.

TABLE 5

| Example No. 1 | Ammonium molybdate, % by mass 2 | Surfactant, % by mass 3 | Malachite green, % by mass 4 | Acid, N 5 | Optical density | |
|---|---|---|---|---|---|---|
| | | | | | in the absence of the virus 6 | in the presence of the virus 7 |
| 9 | 4.5 | Twin-20 0.2 | 0.085 | H$_2$SO$_4$ 5 | 0.089 | 0.782 |
| 10 | 0.75 | Twin-20 0.2 | 0.085 | H$_2$SO$_4$ 5 | 0.058 | 0.561 |
| 11 | 1.5 | Twin-20 0.2 | 0.25 | H$_2$SO$_4$ 5 | 0.148 | 0.881 |
| 12 | 1.5 | Twin-20 0.2 | 0.025 | H$_2$SO$_4$ 5 | 0.050 | 0.557 |
| 13 | 1.5 | Twin-20 0.05 | 0.085 | H$_2$SO$_4$ 5 | 0.086 | 0.851 |
| 14 | 1.5 | Twin-20 0.3 | 0.085 | H$_2$SO$_4$ 5 | 0.028 | 0.502 |
| 15 | 1.5 | Twin-20 0.2 | 0.085 | H$_2$SO$_4$ 3 | 0.069 | 0.516 |
| 16 | 1.5 | Twin-20 0.2 | 0.085 | H$_2$SO$_4$ 7.5 | 0.041 | 0.591 |
| 17 | 1.5 | Sterox 0.2 | 0.085 | H$_2$SO$_4$ 5 | 0.049 | 0.682 |
| 18 | 1.5 | Triton X-305 0.2 | 0.085 | H$_2$SO$_4$ 5 | 0.128 | 0.780 |
| 19 | 1.5 | Twin-20 0.2 | 0.085 | HCl 5 | 0.054 | 0.811 |
| 20 | 1.5 | Twin-20 0.2 | 0.085 | HClO$_4$ 5 | 0.098 | 1.01 |

EXAMPLE 21

Determination of 13 S-globulin of buchwheat seeds

The procedure of Example 7 hereinbefore is repeated, but instead of the virus suspension a solution of 13 S-globulin of the below-specified concentration in a 0.01M buffer of Tris-HCl (pH=7.5) containing 0.1% of Triton X-305 and 0.1% of bovine serum albumin is used. Prior to the addition of the solution of the conjugate, a solution of antibodies specific to 13 S-globulin of buckwheat seeds recovered from rabbit's blood serum in a 0.1M buffer of tris-HCl (pH=7.4) containing 0.1% of Triton X-305 and 0.1% of bovine serum albumine is placed into wells of a microplate for 2 hours at the temperature of 37° C., whereafter the microplate is rinsed with a 0.01M buffer of tris-HCl (pH=7.5) containing 0.15M of NaCl and 0.1% of Triton X-305. The conjugate is obtained as described in Example 6 using antibodies against rabbit's immunoglobulin G recovered from goat's blood serum. As the substrate use is made of non-radioactive sodium pyrophosphate in the concentration of 0.05 mM, while after reaction of the conjugate combined with the surface of a solid phase with the substrate, 0.05 ml of a colour reagent is added which has the composition described in Example 8 hereinbefore.

The values of optical density at 630 nm for a number of concentrations of 13 S-globulin of buckwheat seeds are shown in Table 6 hereinbelow.

TABLE 6

| Concentration of 13 S—globulin of buckwheat seeds, µg/l | Optical density |
| --- | --- |
| 0 | 0.065 |
| 6.7 | 0.132 |
| 20 | 0.281 |
| 60 | 0.589 |

EXAMPLE 22

Determination of mice immunoglobulin G

The procedure of Example 8 is repeated using sodium pyrophosphate in the concentration of 0.05 mM. In the preparation of the conjugate antibodies to mice immunoglobulin G are used which have been recovered from rabbit's blood serum.

The data for a number of mice immunoglobulin G concentrations are shown in Table 7 hereinbelow.

TABLE 7

| Mice immunoglobulin G concentration, µg/ml | Optical density |
| --- | --- |
| 0 | 0.055 |
| 4 | 0.165 |
| 15.6 | 0.339 |
| 31 | 0.563 |
| 62 | 1.37 |

EXAMPLE 23

Determination of the carnation moffle virus disease

The procedure of Example 7 hereinbefore is repeated, but in the preparation of the conjugate use is made of an inorganic pyrophosphatase recovered from baker's yeast; as the substrate use is made of non-radioactive sodium pyrophosphate in the concentration of 0.05 mM and after the reaction of the conjugate combined with the solid phase surface with the substrate 0.05 ml of a colour reagent of the composition of Example 8 is added thereto. The data for some concentrations of the virus of pink mottle disease are shown in Table 8 hereinbelow.

TABLE 8

| Virus concentration, µg/ml | Optical density |
| --- | --- |
| 0 | 0.075 |
| 5 | 0.256 |
| 10 | 0.485 |
| 20 | 0.751 |

What is claimed is:

1. A method for the determination of an antigen in a sample comprising the steps of:
    preparing a conjugate by cross-linking an inorganic pyrophosphatase with antibodies reactive with said antigen to be determined;
    binding any antigen that may be present in said sample to a solid phase;
    reacting a solution of said conjugate with the antigen bound to the solid phase;
    separating the resulting solid and liquid phases;
    reacting one of said solid or liquid phase with a salt of pyrophosphoric acid;
    adding a color reagent to said separated solid or liquid phase;
    wherein the color reagent comprises a strong 3–7.5N inorganic acid containing the following components, % by mass: a salt of molybdic acid-0.75–4.5, a surfactant-0.05–0.3, and malachite green dye-0.025–0.25; determining the presence or the amount of said antigen from the resulting change in color.

2. The method, as in claim 1 wherein the salt of pyrophosphoric acid is used in a concentration of 0.02–0.5 mM.

3. The method as claimed in claim 1, wherein the inorganic pyrophosphatase is isolated from a homogenate of cells of *Escherichia coli* by subjecting said homogenate to a temperature within the range of from 83° to 93° C., followed by chromatography on 1,6-diaminohexylagarose.

* * * * *